US011116393B2

(12) United States Patent
Liu et al.

(10) Patent No.: US 11,116,393 B2
(45) Date of Patent: Sep. 14, 2021

(54) VISION ASSESSMENT BASED ON GAZE

(71) Applicants: AGENCY FOR SCIENCE, TECHNOLOGY AND RESEARCH, Singapore (SG); TAN TOCK SENG HOSPITAL PTE LTD, Singapore (SG)

(72) Inventors: Huiying Liu, Singapore (SG); Augustinus Laude, Singapore (SG); Tock Han Lim, Singapore (SG); Yanwu Xu, Singapore (SG); Wing Kee Damon Wong, Singapore (SG); Jiang Liu, Singapore (SG)

(73) Assignees: AGENCY FOR SCIENCE, TECHNOLOGY AND RESEARCH, Singapore (SG); TAN TOCK SENG HOSPITAL PTE LTD, Singapore (SG)

(*) Notice: Subject to any disclaimer, the term of this patent is extended or adjusted under 35 U.S.C. 154(b) by 190 days.

(21) Appl. No.: 16/090,174

(22) PCT Filed: Mar. 31, 2017

(86) PCT No.: PCT/SG2017/050184
§ 371 (c)(1),
(2) Date: Sep. 28, 2018

(87) PCT Pub. No.: WO2017/171655
PCT Pub. Date: Oct. 5, 2017

(65) Prior Publication Data
US 2019/0110678 A1    Apr. 18, 2019

(30) Foreign Application Priority Data

Mar. 31, 2016    (SG) ............................ 10201602552P

(51) Int. Cl.
*A61B 3/028*    (2006.01)
*A61B 3/113*    (2006.01)
(Continued)

(52) U.S. Cl.
CPC .............. *A61B 3/024* (2013.01); *A61B 3/028* (2013.01); *A61B 3/113* (2013.01); *G16H 40/63* (2018.01); *G16H 50/20* (2018.01)

(58) Field of Classification Search
CPC ....... A61B 3/113; A61B 3/028; A61B 3/0025; A61B 3/0033; A61B 3/0041;
(Continued)

(56) References Cited

U.S. PATENT DOCUMENTS

2009/0091706 A1* 4/2009 Derr ......................... A61B 3/10
  351/205
2015/0164418 A1* 6/2015 Johnson ............... A61B 5/4884
  434/236

FOREIGN PATENT DOCUMENTS

CN    105326471 A    2/2016
GB    2 469 278 A    10/2010
(Continued)

OTHER PUBLICATIONS

PCT International Search Report for PCT Counterpart Application No. PCT/SG2017/050184, 4 pgs. (dated Jun. 19, 2017).
(Continued)

*Primary Examiner* — Brandi N Thomas
(74) *Attorney, Agent, or Firm* — Womble Bond Dickinson (US) LLP

(57) ABSTRACT

The present disclosure generally relates to automated method and system for vision assessment of a subject. The method comprises: determining a set of test patterns for the subject based on a preliminary assessment of an eye of the subject; displaying the set of test patterns sequentially to the subject; collecting data on the subject's gaze in response to each test pattern displayed to the subject; and assessing vision functionality of the subject based on the collected gaze data.

20 Claims, 7 Drawing Sheets

(51) Int. Cl.
    *A61B 3/024*    (2006.01)
    *G16H 40/63*    (2018.01)
    *G16H 50/20*    (2018.01)

(58) Field of Classification Search
    CPC ....... A61B 3/0091; A61B 3/085; A61B 3/102;
            A61B 3/117; A61B 3/18; A61B 5/0066;
            A61B 5/0073; A61B 3/024; A61B 3/032;
            A61B 5/121; A61B 5/14542; A61B 5/16;
                    A61B 5/4884; A61B 5/742
    USPC ........ 351/200, 205–206, 209–211, 221–223,
                                    351/243–246
    See application file for complete search history.

(56)            References Cited

FOREIGN PATENT DOCUMENTS

WO      WO 00/72745 A1      12/2000
WO      WO 02/00105 A1      1/2002
WO      WO 2011/109297 A1   9/2011

OTHER PUBLICATIONS

PCT Written Opinion for PCT Counterpart Application No. PCT/SG2017/050184, 5 pgs. (dated Jun. 19, 2017).
Z. Zhang, et al., "A survey on computer aided diagnosis for ocular diseases," BMC Medical Informatics and Decision Making, vol. 14, No. 80, pp. 1-29 (Aug. 31, 2014).

* cited by examiner

VISION ASSESSMENT BASED ON GAZE

CROSS-REFERENCE TO RELATED APPLICATIONS

This patent application is a U.S. National Phase Application under 35 U.S.C. § 371 of International Application No. PCT/SG2017/050184, filed on 31 Mar. 2017, entitled VISION ASSESSMENT BASED ON GAZE, which claims the benefit of Singapore Patent Application No. 10201602552P, filed on 31 Mar. 2016, which was incorporated in its entirety by reference herein.

TECHNICAL FIELD

The present disclosure generally relates to vision assessment based on gaze. More particularly, the present disclosure describes various embodiments of an automated method and system for vision assessment of a subject (e.g. human patient or candidate).

BACKGROUND

Vision assessments are used to assess vision/visual functionality and impairment. The assessment of vision/visual symptoms is important for the detection, monitoring, and screening of eye/ocular conditions/diseases, such as macular degeneration. A vision assessment will alert a person, e.g. a subject or patient, to any changes that may indicate a problem or a worsening of a condition/disease. There are various methods/procedures/tests to assess the vision of a subject, such as based on the subject's gaze. Existing studies have shown that gazes of subjects with impaired vision are different from subjects with normal vision.

A first method or test the Amsler grid for monitoring a subject's central visual field. The Amsler grid is a tool for detecting vision problems resulting from damage to the macula or optic nerve, which may be caused by macular degeneration. For example, the subject's eyes may be screened and monitored to detect the onset of age-related macular degeneration (AMD). In this test, the subject is required to stare at the central dot of the Amsler grid and to report the missing or distortion of the grid lines. However, it may be difficult to ensure compliance with the testing procedures, reporting, and recording of test findings. Moreover, elderly subjects may find it difficult to maintain fixation on the central dot, thus affecting the accuracy of the test.

A second test is preferential hyperacuity perimetry (PHP), which is a psychophysical test used to identify and quantify visual abnormalities such as metamorphopsia and scotoma. The PHP test is based on visual hyperacuity or Vernier acuity—ability to identify the misalignment of visual objects or target features. The PTP test requires a subject to fixate on a central point and indicating on a screen at the perceived location of a misaligned dot. This has been shown to be more sensitive than the Amsler grid test in detecting visual changes associated with AMD, although this may be at a cost of less specificity. However, devices for the PHP test are costly and bulky.

A third test is entoptic perimetry (EP). Noise field campimetry can help subjects to perceive a scotoma because of perceptual filling-in. For example, the EP test may require a subject to stare at a screen displaying visual noise patterns, such as black and white spots flickering randomly or the static produced by a conventional television tuned to a non-transmitting station. The region of the scotoma is perceived as a motionless or dark/grey area, different from the rest.

A fourth test is microperimetry (MP) or fundus related perimetry. MP is a type of visual field test that creates a retinal sensitivity map of light perceived in parts of the retina. The MP test requires a subject to fixate on a cross at the centre of a test pattern or test image. A dot then appears in the vision field. The subject is instructed to press a button if he/she notices the appearance of the dot. The intensity of the dot at a position may change adaptively, e.g. increase to a necessary intensity, in order for the subject to notice the dot.

There are some problems associated with one or more of the current methods or tests for vision assessment. The tests require the subjects to undergo the same procedures, but some subjects may require different tests or procedures according to their different vision conditions. Having a standard test for all subjects may not be effective for accurate vision assessment of the subjects. Furthermore, in the tests, the subjects are required to fixate on a target throughout. Lack of fixation due to fatigue or other factors may compromise the test results and make them unreliable. There is also significant manual work required for the tests. Particularly, the tests require the presence of trained personnel, e.g. a doctor or ophthalmologist, while the tests are being conducted. For the subjects, they need to provide manual responses or oral reports, which may be challenging for the elderly and can the test results obtained may also be highly subjective.

Therefore, in order to address or alleviate at least one of the aforementioned problems and/or disadvantages, there is a need to provide an automated method and system for vision assessment of a subject, in which there is at least one improvement and/or advantage over the aforementioned prior art.

SUMMARY

According to an aspect of the present disclosure, there is an automated method and system for vision assessment of a subject. The system comprises a processor configured for performing steps of the method. Steps of the method comprise: determining a set of test patterns for the subject based on a preliminary assessment of an eye of the subject; displaying the set of test patterns sequentially to the subject; collecting data on the subject's gaze in response to each test pattern displayed to the subject; and assessing vision functionality of the subject based on the collected gaze data.

An advantage of the present disclosure is that the test patterns are customized/personalized for the subjects according to his/her conditions and/or requirements. The method and system are automated such there is no need for verbal communication or manual response from the subject, thereby producing more objective results. Less manual effort is required from the subject so there is less fatigue caused to the subject, making it more relaxing for the subject to undergo vision assessment. Furthermore, the method/system can be operated easily by a trained nurse instead of a doctor or ophthalmologist, resulting in time and labour savings of the clinicians if the method/system is implemented in a medical facility.

An automated method and system for vision assessment of a subject according to the present disclosure are thus disclosed herein. Various features, aspects, and advantages of the present disclosure will become more apparent from the following detailed description of the embodiments of the

DETAILED DESCRIPTION

In the present disclosure, depiction of a given element or consideration or use of a particular element number in a particular figure or a reference thereto in corresponding descriptive material can encompass the same, an equivalent, or an analogous element or element number identified in another figure or descriptive material associated therewith. The use of "/" in a figure or associated text is understood to mean "and/or" unless otherwise indicated. As used herein, the term "set" corresponds to or is defined as a non-empty finite organization of elements that mathematically exhibits a cardinality of at least one (e.g. a set as defined herein can correspond to a unit, singlet, or single element set, or a multiple element set), in accordance with known mathematical definitions. The recitation of a particular numerical value or value range herein is understood to include or be a recitation of an approximate numerical value or value range.

For purposes of brevity and clarity, descriptions of embodiments of the present disclosure are directed to an automated method and system for vision assessment of a subject, in accordance with the drawings. While aspects of the present disclosure will be described in conjunction with the embodiments provided herein, it will be understood that they are not intended to limit the present disclosure to these embodiments. On the contrary, the present disclosure is intended to cover alternatives, modifications and equivalents to the embodiments described herein, which are included within the scope of the present disclosure as defined by the appended claims. Furthermore, in the following detailed description, specific details are set forth in order to provide a thorough understanding of the present disclosure. However, it will be recognized by an individual having ordinary skill in the art, i.e. a skilled person, that the present disclosure may be practiced without specific details, and/or with multiple details arising from combinations of aspects of particular embodiments. In a number of instances, well-known systems, methods, procedures, and components have not been described in detail so as to not unnecessarily obscure aspects of the embodiments of the present disclosure.

Figure 1A:
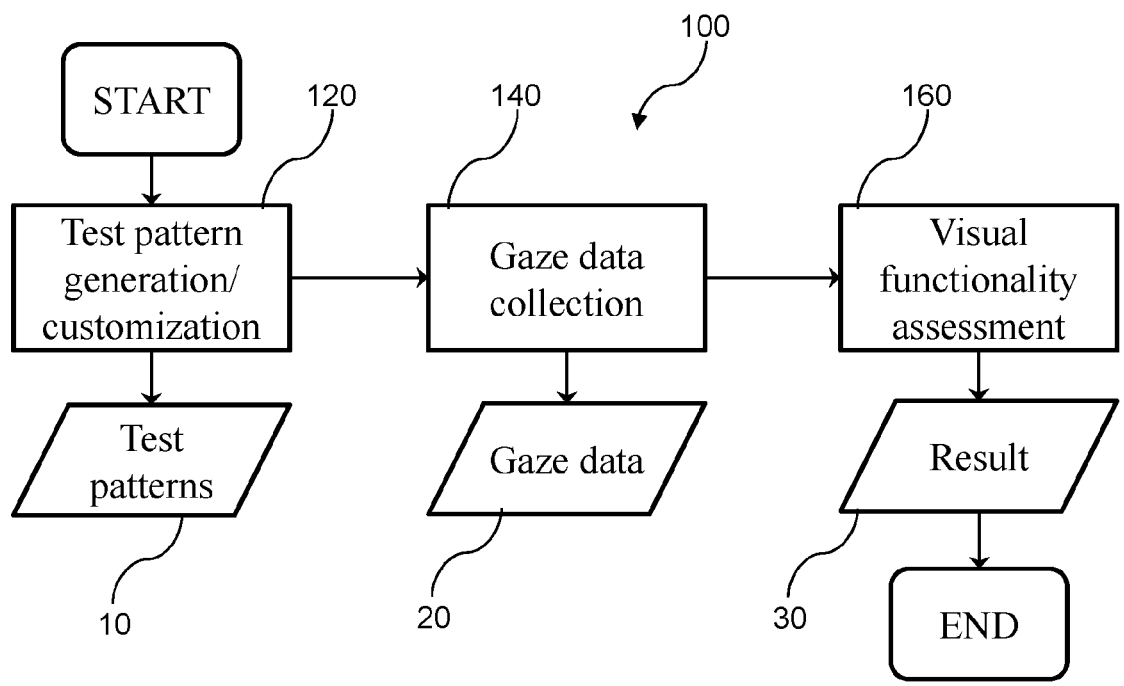
FIG. 1A illustrates a flowchart of an automated method for vision assessment of a subject.

In representative or exemplary embodiments of the present disclosure, with reference to FIG. 1A, there is an automated method 100 for vision assessment of a subject. Broadly, the method 100 includes a step/process 120 of determining a set of test patterns 10 for the subject based on a preliminary or initial assessment of an eye of the subject. The set of test patterns 10 are thus generated and customized/personalized for each subject according to the preliminary assessment. The step/process 120 may otherwise be referred to as the "test pattern customization" process. The set of test patterns 10 are then displayed to the subject sequentially, i.e. one test pattern 10 at a time. The method 100 includes a step/process 140 of collecting data 20 on the subject's gaze in response to each test pattern 10 displayed to the subject. A gaze may be defined as a steady/intense look at the test pattern 10 or a portion thereof. The step/process 140 may otherwise be referred to as the "gaze data collection" process. The method 100 includes a step/process 160 of assessing vision functionality (or in other words assessing vision impairment) of the subject based on the collected gaze data 20, thereby obtaining a vision assessment result 30. The step/process 160 may otherwise be referred to as the "visual functionality assessment" process.

Figure 1B:
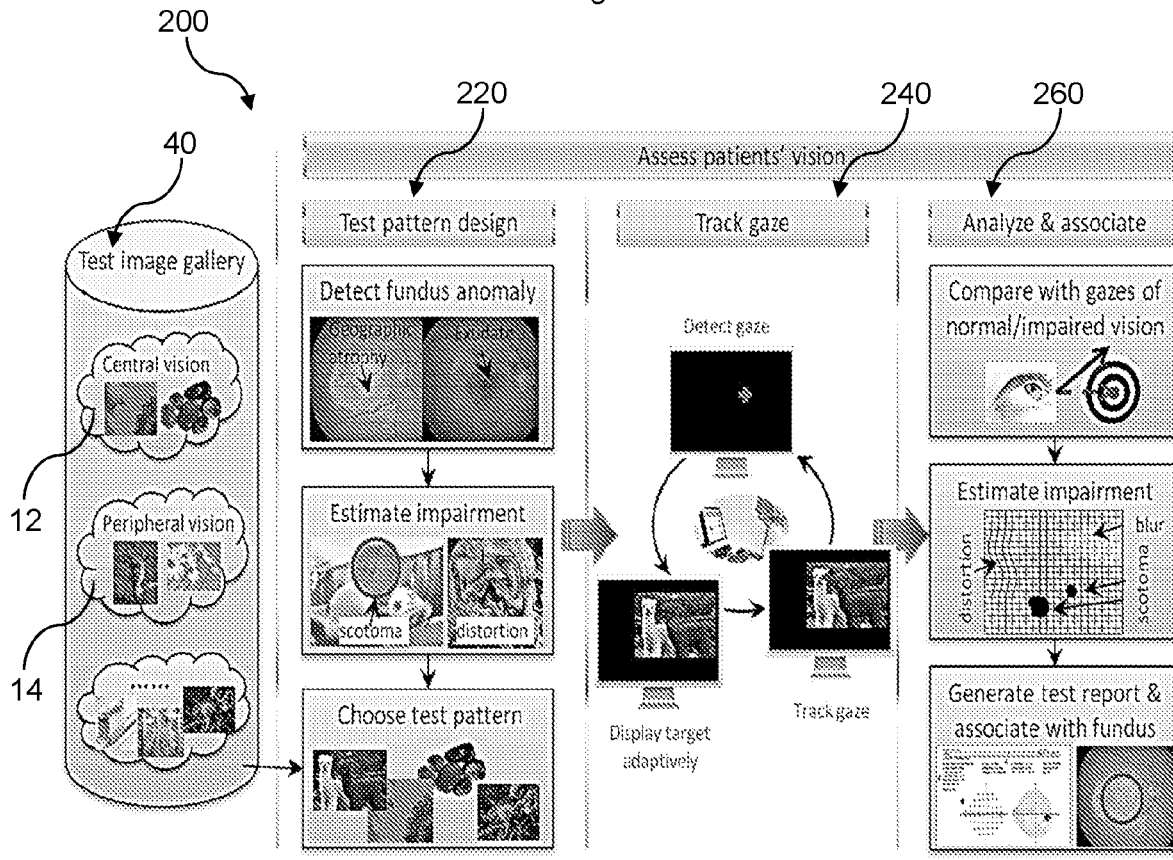
FIG. 1B illustrates a system for vision assessment of the subject.

As shown in FIG. 1B, there is a system 200 including a processor for performing the automated method 100. The system 200 is also referred to as a system for Automated Vision Assessment and Impairment Detection through Gaze Analysis (AVIGA). The system 200 includes various stages or phases for performing various steps/processes of the method 100. Broadly, the system 200 includes a first stage 220 or the "test pattern design" stage for performing the process 120, a second stage 240 or the "track gaze stage" for performing the process 140, and a third stage 260 or the "analyze & associate" stage for performing the process 160. It will be appreciated that the vision assessment by the method 100 and system 200 may be performed on the subject one eye at a time.

Figure 2A:
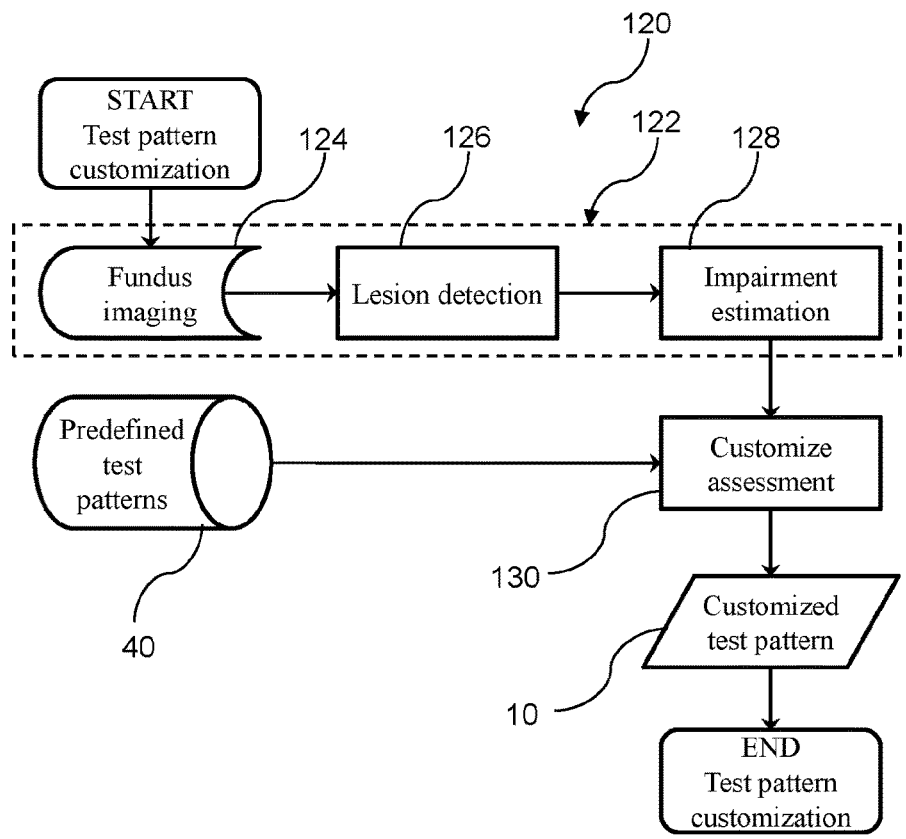
FIG. 2A illustrates a flowchart of a test pattern customization process in the automated method for vision assessment of the subject.

With reference to FIG. 2A, the process 120 performed during the first stage 220 includes a number of steps. The process 120 includes a preliminary assessment 122 of the subject's eye, the preliminary assessment 122 including assessing a fundus of the eye. The fundus of the eye is the interior surface of the eye opposite the lens and includes the retina, optic disc, macula, fovea, and posterior pole. The preliminary assessment 122 includes a step 124 of imaging the fundus of the eye, a step 126 of analyzing the fundus image to detect damage and/or anomalies in the eye, such as presence of lesions of the retina, and a step 128 of estimating vision impairment of the subject based on the fundus analysis. Detected lesions can be used to estimate the type, size, and location of vision impairments.

Based on individual requirements derived from the fundus analysis and estimated vision impairment, in a step 130 of the process 120, a vision assessment test can be customized/personalized for the subject. Specifically, the customization includes determining or selecting the set of test patterns or images 10 from a pattern database 40 of predefined test patterns. The selected set of test patterns 10 may also be referred to as customized/personalized test patterns 10 for the subject. Referring to FIG. 1B, the pattern database 40 is a gallery of a global set of predefined test patterns/images that are suitable for assessing vision functionality/impairment of subjects due to various conditions/diseases. For example, there are predefined test patterns 12 suitable for assessing central vision of subjects, and other predefined test patterns 14 suitable for assessing peripheral vision of subjects. In one embodiment, the subject is detected/diagnosed with geographic atrophy, a late stage of the dry form of AMD, based on the preliminary assessment 122. Vision functi9onality/impairment due to geographic atrophy can be assessed by predicting a scotoma near the center of the vision field. Customized test patterns 10 suitable for scotoma assessment (e.g. based on size/position), can be selected from the pattern database 40 for the subject.

Figure 2B:
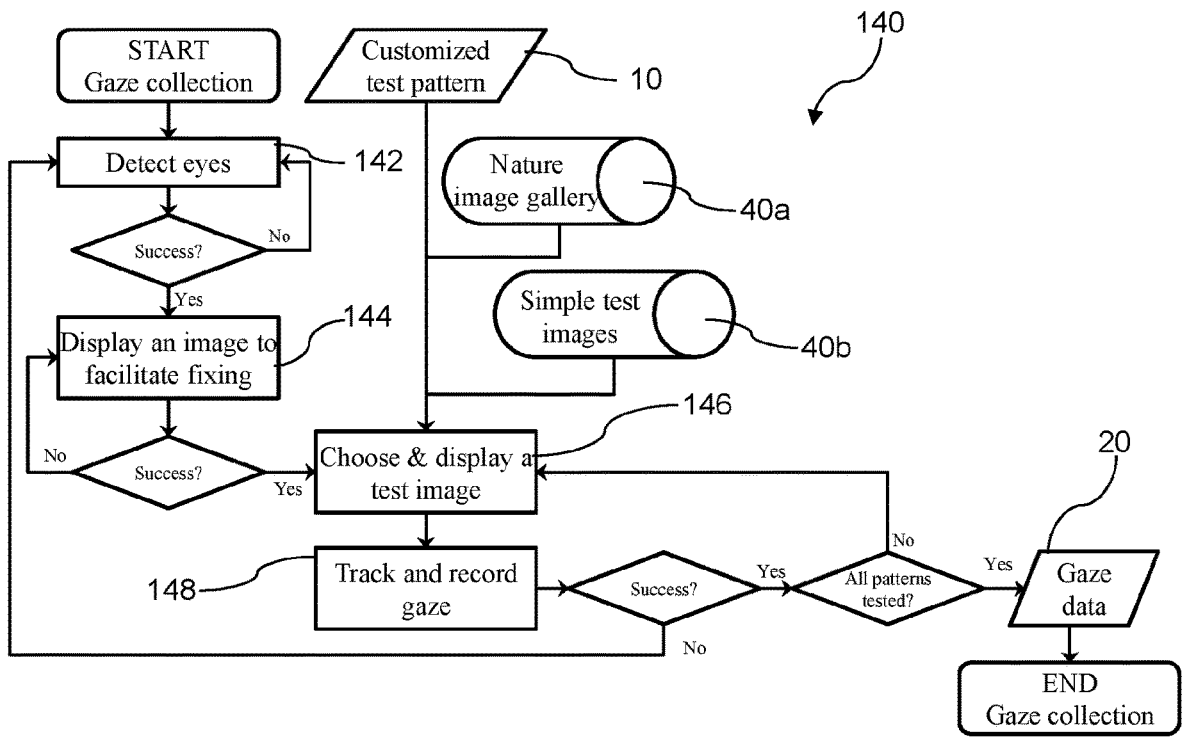
FIG. 2B illustrates a flowchart of a gaze data collection process in the automated method for vision assessment of the subject.
Figure 2C:
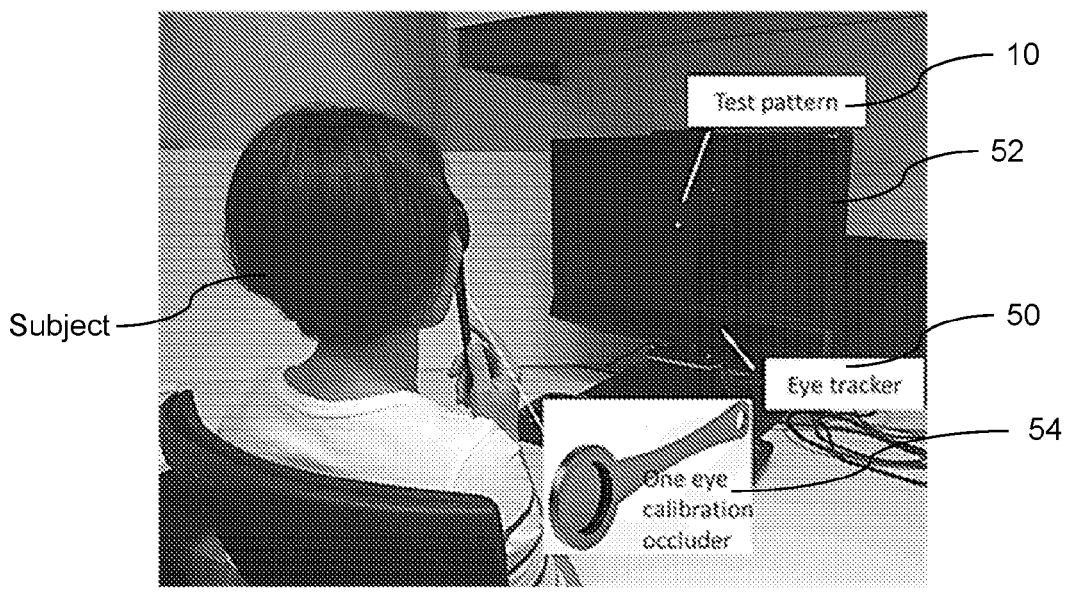
FIG. 2C illustrates the positioning of the subject during the vision assessment.

With reference to FIG. 2B, the process 140 performed during the second stage 240 includes a number of steps. The process 140 includes a step 142 of detecting the eyes of the subject. An eye tracker machine may be used to detect the eyes and collect the gaze data 20. As shown in FIG. 2C, the subject is seated in front of there is an eye tracking machine or eye tracker 50, e.g. a Tobii eye tracking machine TX300. The test patterns 10 are displayed on a screen 52 to the subject and the subject's gaze in response to each test pattern 10 is tracked by the eye tracker 50. As the gaze data 20 is collected one eye at a time, i.e. monocular eye tracking, an infrared transparent occluder 54 is used to cover one eye.

If the subject's eyes cannot be detected in the step 142, the subject may be requested to adjust his/her seating position and/or head position. The step 142 is repeated until the eye tracker 50 detects the eyes. Once the eyes are successfully detected, a set of patterns/images are displayed to the subject to facilitate fixing. This may also be referred to as a calibration process 144 for calibrating the eye tracker 50 specifically to this subject. After the calibration process 144 has been successfully completed, the set of customized test patterns 10 are displayed to the subject. As described above, the customized test patterns 10 are determined from the pattern database 40. In addition to categorizing the predefined test patterns in the pattern database 40 according to suitability to types of vision assessment, the pattern database 40 may categorize the predefined test patterns based on graphics in the test patterns. For example, the pattern database 40 may include a group 40a of predefined test patterns with graphics associated with nature, and a group 40b of predefined test patterns with simple graphics.

In a step 146, the customized test patterns 10 are sequentially selected and displayed to the subject. In a step 148, the subject's gaze in response to each customized test pattern 10 is tracked and recorded by the eye tracker 50. Each customized test pattern 10 is displayed to the subject for a predefined duration while the subject's gaze is being tracked and the gaze data 20 is being collected. The eye tracker 50 is able to work at a high frequency to track the gaze in real time. The high speed makes it possible to display the customized test patterns 10 adaptively according to the current position of the subject's gaze. Accordingly, the subject is not required to fixate his/her eye on a single position for the entirety of the process 140, i.e. there is no requirement for central fixation in the method 100/system 200.

The steps 146 and 148 are iterated until all the customized test patterns 10 are displayed and the gaze data 20 is collected successfully. In some situations, the eye tracker 50 may not be able to track the subject's gaze in response to one or more test patterns 10. This may be due to failure to detect the eyes for obtaining the gaze data 20. In these situations, the step 142 may be repeated to detect the eyes again and to recalibrate the eye tracker 50.

Figure 2D:
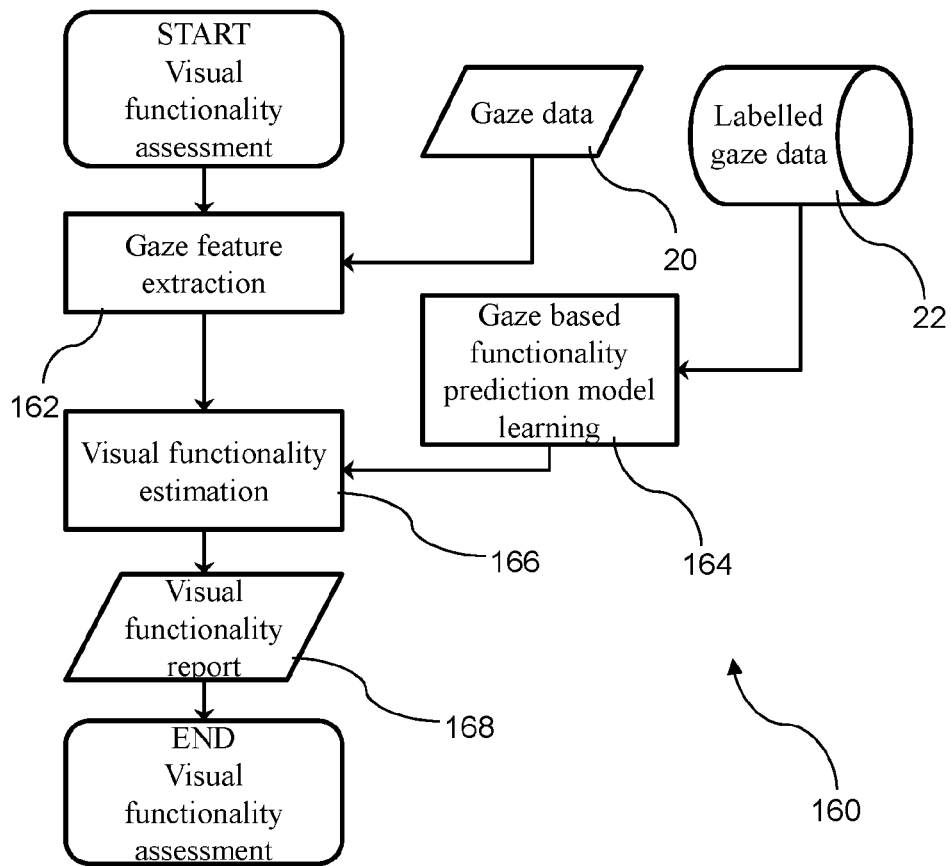
FIG. 2D illustrates a flowchart of a visual functionality assessment process in the automated method for vision assessment of the subject.

With reference to FIG. 2D, the process 160 performed during the third stage 260 includes a number of steps. The process 160 includes a step 162 of extracting gaze features from the gaze data 20. In addition, there is an existing database of gaze data associated with a population of subjects/patients, including subjects with normal vision and subjects with impaired vision. This database may also be referred to as a subject database storing labelled gaze data 22, wherein the labelled gaze data 22 serves as a basis for comparison with the collected gaze data 20 from the process 140. In a step 164, the labelled gaze data 22 is used to train a gaze-based functionality prediction model, e.g. by machine learning.

The process 160 includes a step 166 of comparing the gaze data 20 with the subject database to generate a visual/vision functionality estimation. Specifically, in the step 166, the gaze features extracted from the gaze data 20 are analyzed and compared to the labeled gaze data 22 in the subject database in order to determine whether there is any correlation/association between the gaze data 20 and the existing labeled gaze data 22. The gaze-based functionality prediction model estimates the visual/vision functionality of the subject based on the analysis of the gaze data 20. In a step 168, results of the visual/vision functionality estimation is generated in a visual/vision functionality or assessment report or result 30. The vision assessment report 30 provides details on, but not limited to, the type, size, degree, and position of the vision impairment, as well as the correlation/association with anomalies of the fundus.

Therefore, the automated method 100 and system 200 are configured for performing vision assessment of a subject. The vision assessment may be affected by some factors. Firstly, the freedom of movement of the subject's head may affect the vision assessment results 30. Secondly, the elimination of central fixation (as described above in the process 140) may affect the vision assessment results 30. The impact of each of these factors may be tested in initial implementation tests of the method 100/system 200. In these implementation tests, test patterns 10 following that of microperimetry (MP) are used. Specifically, the test patterns 10 are white dots on a black background, as shown in FIG. 3A to FIG. 3D.

Figure 3A:
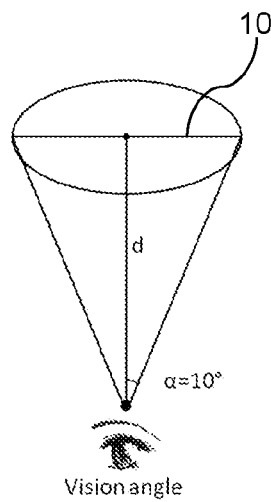
FIG. 3A to FIG. 3D illustrate various views of a test pattern for vision assessment of the subject.
Figure 3B:
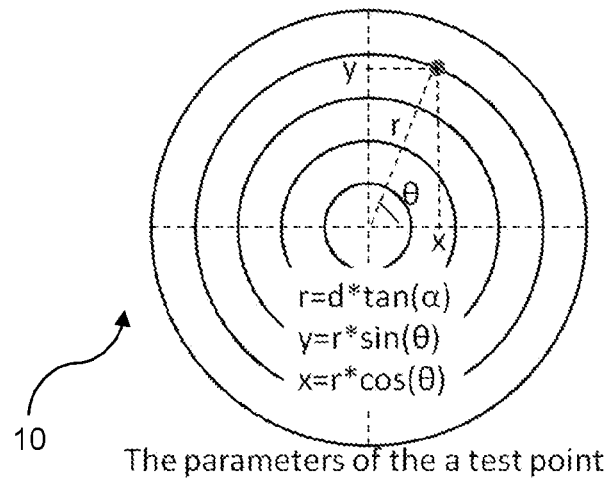
Figure 3C:
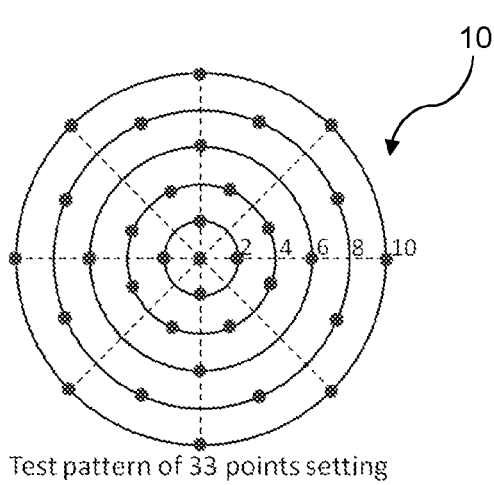

The position of a target/test dot on the test pattern 10 is determined according to the position of the eye E, current gaze position G, and the position ($\alpha$, $\theta$) in the vision field to be tested. When both the position of eye and the position of the gaze are specified and fixed, the line between the two eyes are horizontal, and the line of sight is perpendicular to the screen, the determination of the position of the dot is simpler. Referring to FIG. 3A, d is the distance from the eye to the screen 52. Referring to FIG. 3B, on the screen 52, the distance from the test dot to the gaze position is $r=d\times\tan\alpha$. Let $\theta$ be the angle to the horizontal line. The position of the test dot, relative to the centre point/dot of the test pattern 10, is defined as $x=r\times\cos\theta$ and $y=r\times\sin\theta$. Referring to FIG. 3C, the test pattern 10 shows all 33 test points/dots relative to the centre point/dot.

The impact of the freedom of movement of the subject's head is assessed in a first implementation test. When the positions of the head, eye, and/or gaze are free to move, the following steps are taken to determine the position of the test dot. As shown in Step 1 of FIG. 4A, the tilting angle of the head is calculated using the positions of the two eyes ($\varphi$). In Step 2 of FIG. 4A, the minimum and maximum distances from the test dot to the gaze position are calculated. These two extreme distances on the straight line connecting E' (the projection of the eye on the plane of the screen 52) and G. Let d be the distance from the eye to the screen, and β be the angle between EE' and EG. Then, the minimum distance is $r_1 = d \times \tan(\beta) - d \times \tan(\beta-\alpha)$ and the maximum distance is $r_2 = d \times \tan(\alpha+\beta) - d \times \tan(\beta)$. Let the position of the test dot be $P=(x, y, 0)^T$, where $x = r \cos(\theta+\varphi)$ and $y = r \sin(\theta+\varphi)$. The position of the test dot can be determined by optimizing $$r = \underset{r}{\mathrm{argmin}} \frac{\vec{EP} \cdot \vec{EG}}{|\vec{EP}| \times |\vec{EG}|} - \cos(\alpha).$$

Figure 4A:
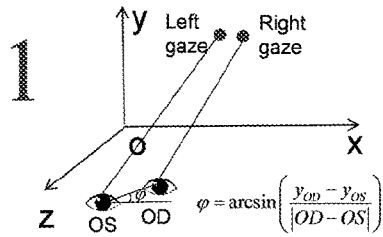
FIG. 4A illustrates a first implementation test on impact on the vision assessment due to movement of the subject's head.
Figure 4A:
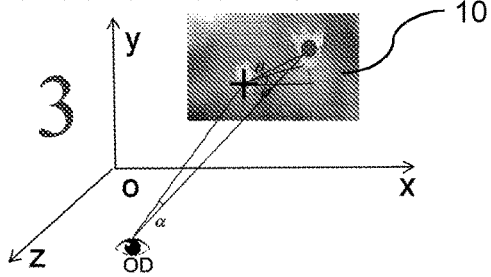
Figure 4A:
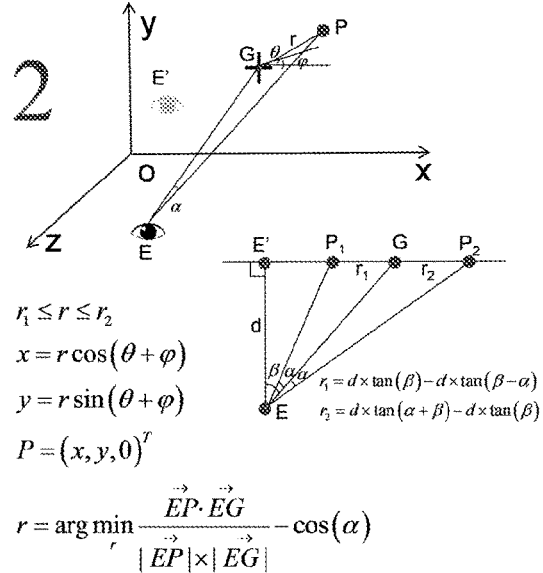

Step 3 of FIG. 4A shows one embodiment of the first implementation test. Each test dot is round with a radius of 0.13 centimetres. The size of the screen 52 used for eye tracking is 50.92 cm×28.64 cm, and the resolution of the screen 52 is 1920×1080. Thus, the size of a pixel is 0.0265 cm, and the size of the test dots in terms of pixels is 0.13/0.0265×2+1=11 pixels.

In the first implementation test, to measure the impact of free head movement on the vision assessment results 30, the performance of the system 200 is compared between the settings with free head position and with fixed/rigid head position. This comparison is performed by using blind spot detection. The first implementation test detects the blind spot of the right eye. The eccentricities are {12°, 13°, . . . , 20°}. The vision angles range from −20° to 20°. At each eccentricity, a 4-2-1 scheme is adopted to search for the boundary of the blind spot. The 4-2-1 scheme means the step length is first set as 4 to find the coarse boundary. The step length is then set as 2 to find a finer boundary. Finally, the step length is set as 1 to find the exact boundary. During the first implementation test, the subject is required to fix on a cross and press any key (on a computer input device) to indicate that he/she has noticed the test dot.

The workflow of the first implementation test having the setting with free head position is as follows.
  a. The subject is seated before the eye tracker 50.
  b. The eye tracker 50 tracks the position of the eyes and gaze in real time.
  c. Display a test pattern with a cross positioned at the current position of the gaze to help the subject to fixate on the test pattern.
  d. Choose a position of the vision field to be tested.
  e. Determine the position of the test dot, according to the positions of the eye and gaze.
  f. Display the test dot at the position obtained from step (d). The test dot is displayed at a different position from the cross in step (c).
  g. Maintain the display of the test pattern for a predefined duration.
  h. The subject presses a key/button if he/she notices the appearance of the test dot.
  i. The test is ended after all the positions of the test dots have been tested. If not, return to step (b) and continue.

The workflow of the first implementation test having the setting with fixed head position is as follows.
  a. The subject is seated before the eye tracker 50. The subject adjusts his/her position to make sure that the eyes are facing at nearly the centre of the screen 52.
  b. Display a test pattern with a cross to help the subject to fixate on the test pattern. The position of the cross will ensure that the line between the eyes and the gaze is perpendicular to the screen 52.
  c. The subject is required to keep his/her head fixed/stationary during the test.
  d. Choose a position of the vision field to be tested.
  e. Determine the position of the test dot, according to the positions of the eye and gaze.
  f. Display the test dot at the position obtained from step (e). The test dot is displayed at a different position from the cross in step (b).
  g. Maintain the display of the test pattern for a predefined duration.
  h. The subject presses a key/button if he/she notices the appearance of the test dot.
  i. The test is ended after all the positions of the test dots have been tested. If not, return to step (d) and continue.

Figure 4B:
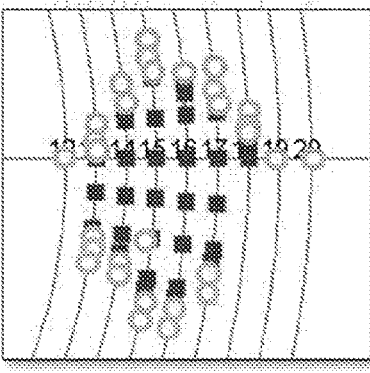
FIG. 4B illustrates results of the first implementation test between free head position and fixed head position settings.
Figure 4B:
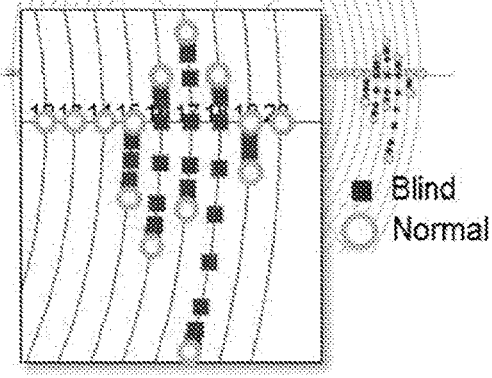

FIG. 4B illustrates the comparison results between the free head position and fixed head position settings. It can be seen from the results that free head position may cause some noise compared to fixed head position. Accordingly, it would be advantageous to perform the method 100 with the system 200 under the fixed head position setting.

The impact of the elimination of central fixation is assessed in a second implementation test. In the second implementation test, to measure the impact of the elimination of central fixation on the vision assessment results 30, the performance of the system 200 is compared between the settings without central fixation and with central fixation. For this comparison, central vision assessment is adopted as an example and the assessment results from MP are used as ground truth. For consistency with MP, a test pattern 10 with 33 test dots is used, such as shown in FIG. 3C. The vision angles tested are α={0°, 2°, 4°, 6°, 8°, 10°}, and the positions tested are θ={0°, 22.5°, 45°, 67.5°, . . . , 337.5°}.

Figure 5A:
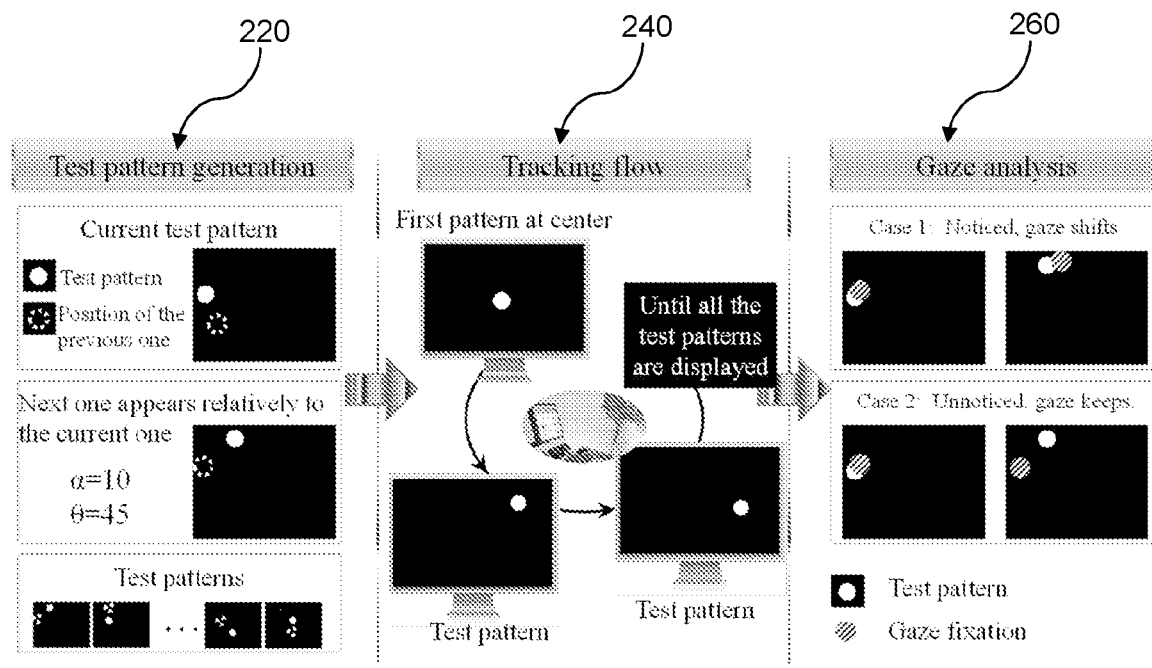
FIG. 5A illustrates a second implementation test on impact on the vision assessment due to elimination of central fixation.

FIG. 5A illustrates the workflow of the second implementation test having the setting without central fixation. Under this setting, a first test pattern with a cross at the centre is displayed to the subject, and the subject is required to fixate on the cross. A second test pattern with a test target or test dot then appears. If the subject notices the target, he/she shifts the gaze to the target and fixates on it. If the subject does not notice the target, he/she keeps fixating on the cross of the first test pattern. The first test pattern with the cross then disappears and a third test pattern with a cross appears in place of the first test pattern. The cross of the third test pattern is positioned at the target of the second test pattern and serves as the next fixation point for the subject. In other words, the centre cross for the current test pattern is positioned based on the target of the previous test pattern. The steps are iterated until all the test patterns with test targets have been displayed. The test patterns with test targets are displayed in a random sequence to avoid the effect of anticipation. Each test pattern is displayed twice to ensure the robustness of the second implementation test. For test patterns with 33 test targets, there are in total 33×2+1=67 test patterns displayed. Each test pattern is displayed for 2 seconds so the test takes around 2 to 3 minutes to complete.

Figure 5B:
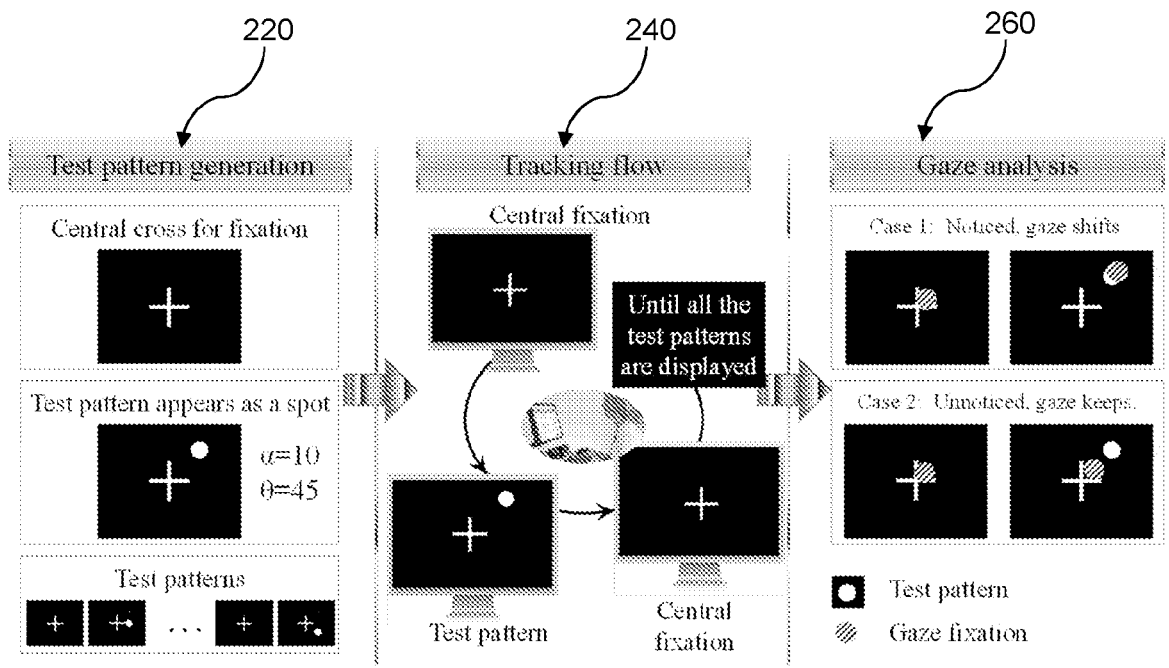
FIG. 5B illustrates a second implementation test on impact on the vision assessment due to central fixation.

FIG. 5B illustrates the workflow of the second implementation test having the setting with central fixation. Under this setting, a first test pattern with a cross at the centre is displayed to the subject, and the subject is required to fixate on the cross. A second test pattern with a test target or test dot then appears. If the subject notices the target, he/she shifts the gaze to the target and fixates on it. If the subject does not notice the target, he/she keeps fixating on the cross of the first test pattern. The second test pattern with the target then disappears and the subject shifts the gaze back to (or maintains the gaze at) the cross of the first test pattern. The steps are iterated until all the test patterns with test targets have been displayed. The test patterns with test targets are displayed in a random sequence to avoid the effect of anticipation. Each test pattern is displayed twice to ensure the robustness of the second implementation test. For test patterns with 33 test targets, there are in total 33×2×2−1=131 test patterns displayed. Each test pattern is displayed for 2 seconds so the test takes around 4 to 5 minutes to complete.

In both settings and for each test pattern, there are three types of results as follows.
  i. The subject failed to fixate on the central cross (or test target of previous test pattern), or the eye tracker 50 failed to track the fixation on the central cross/test target. In this situation, the assessment of this test pattern is deemed to be invalid.
  ii. The subject successfully fixated on the central cross (or test target of previous test pattern) but did not fixate on the test target. This situation means the subject did not notice the appearance of the test target and may indicate vision scotoma.
  iii. The subject successfully fixated on the central cross (or test target of previous test pattern) and successfully fixated on the test target.

Figure 5C:
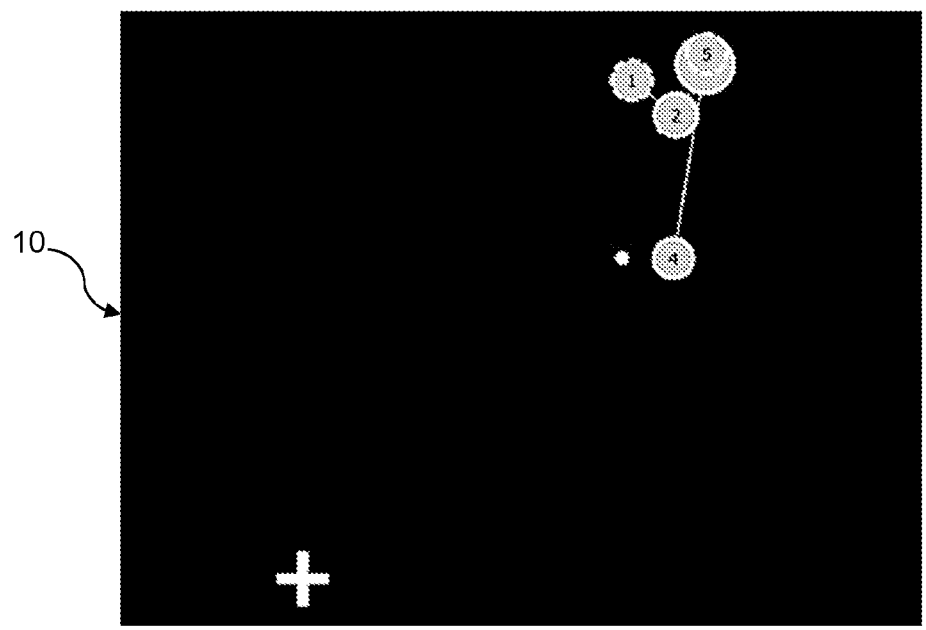
FIG. 5C illustrates a test pattern with multiple fixations.

The second implementation test is thus dependent on whether the subject noticed the test targets. Notably, when the subject is fixating on a central cross or test target, the subject's gaze may shift a little. The eye tracker 50 may also have some error, such as due to manufacturing reasons. As a result, there may be more than one fixation on one cross/test target, as shown in FIG. 5C. These multiple fixations are marked as $F_1, F_2, \ldots, F_n$, with n being the total number of fixations during the display of each test pattern. In one embodiment, the average of five fixations nearest the test target is taken to determine fixation on the target. In order to determine whether the subject noticed the test target, a threshold of 200 pixels is used for this determination. If the distance from the fixation to the target is smaller than 200 pixels, the test target (or central cross) is deemed to be noticed. If at least one fixation is focused on the test target, the test target is deemed to be noticed. Thus, the fixations are marked as either success or failure.

For the valid and successfully noticed test targets, four features from the test patterns with the noticed test targets are concatenated to estimate the vision functionality at the positions of the noticed test targets. Support vector regression with radial basis kernel function is employed for determining the four features listed below.
  i. Acting time—The time taken to shift the gaze from the previous test target (or central cross) to the current test target. It is calculated as the difference between start time of the first successful fixation and the start time of the displaying of the test pattern.
  ii. Fixation duration—The total duration all the successful fixations on the test targets.
  iii. Accuracy—The average distance of the successful fixations from the actual test target to the one measured by the eye tracker 50.
  iv. Precision—The spatial variation of the position of the gaze calculated using all the successful fixations.

The results from the second implementation test are compared with MP to determine the performance difference between the setting without central fixation and the setting with central fixation, thereby evaluating the method 100/system 200. MP data may be obtained using a NIDEK MP-1 microperimeter. The value ranges from 0 to 20, with 0 indicating the subject cannot see at all and 20 indicating the subject has excellent vision functionality. The built-in refractive error correction function in the microperimeter is employed so no subjects wore contact lens during the microperemetry data collection.

Seven subjects were chosen to participate in the second implementation test. The subjects have normal vision or refraction error. While taking the MP test, the built-in refractive error correction function is employed. While taking the second implementation test with both settings (with and without central fixation), two subjects wore contact lens, while the rest did not have their refraction errors corrected. The subjects are aged from 30 to 35. Details of the subjects are shown in Table 1 below.

TABLE 1

| Subject | Gender | Refraction error of right eye | Refraction error of left eye | Wearing contact lens? |
|---|---|---|---|---|
| P1 | Male | −2.0 | 1.5 | No |
| P2 | Male | −4.5 | −4.5 | Yes |
| P3 | Female | −5.5 | −5.0 | Yes |
| P4 | Male | −3.0 | −3.0 | No |
| P5 | Male | −2.5 | −2.5 | No |
| P6 | Female | 0.0 | 0.0 | No |
| P7 | Female | −1.0 | −1.0 | No |

A leave-one-out scheme is used to evaluate the performance of the system 200. At each time, one subject is chosen as test data and the others are used as training data. The left eye and right eye are analyzed separately.

Mean error is used to evaluate the performance of the system 200. This mean error refers to the absolute difference between the estimated value and the ground truth (MP). For each eye, the mean error is calculated for all the valid test patterns. The lower the mean error is, the better the performance of the system 200 is. The calculated mean errors are measured against the mean error of the MP itself, which is calculated as 3.0 in this case. Table 2 shows the results of the second implementation test with both settings (with and without central fixation). Particularly, Table 2 shows the calculated mean errors obtained for each eye of each subject where available.

TABLE 2

| Subject | Eye | Mean error (without central fixation) | Mean error (with central fixation) |
|---|---|---|---|
| P1 | OD (oculus dextrus)/Right | N/A | N/A |
| P1 | OS (oculus sinister)/Left | 2.27 | 2.96 |
| P2 | OD (oculus dextrus)/Right | N/A | N/A |
| P2 | OS (oculus sinister)/Left | 1.60 | 1.25 |
| P3 | OD (oculus dextrus)/Right | 1.84 | 1.55 |
| P3 | OS (oculus sinister)/Left | 2.72 | 2.86 |
| P4 | OD (oculus dextrus)/Right | 1.58 | 1.99 |
| P4 | OS (oculus sinister)/Left | 2.04 | 1.74 |
| P5 | OD (oculus dextrus)/Right | 2.64 | 3.41 |
| P5 | OS (oculus sinister)/Left | N/A | N/A |
| P6 | OD (oculus dextrus)/Right | 1.88 | 1.66 |
| P6 | OS (oculus sinister)/Left | 1.66 | 2.68 |
| P7 | OD (oculus dextrus)/Right | 4.04 | 4.48 |
| P7 | OS (oculus sinister)/Left | 2.44 | 2.47 |
|  | Average | 2.25 | 2.46 |

From Table 2, it can be seen that the average mean error of the setting without central fixation is 2.25, lower than that of the setting with central fixation (2.46). We can also see that the mean error is lower than the one of MP (3.0). Thus, the setting without central fixation obtains better performance in means of lower precision. This is because this setting takes a shorter time than the setting with central fixation. In this second implementation test, the setting without central fixation took 2 minutes 14 seconds while the setting with central fixation took 4 minutes 22 seconds). Due to the shorter duration, the setting without central fixation causes less fatigue to the subjects.

Therefore, based on results from the first and second implementation tests, the vision assessment results 30 would be impacted by free movement of the subject's head and use of central fixation. In order to achieve more accurate vision assessment results 30, embodiments of the automated method 100 and system 200 require the subject to position his/her head in a fixed/rigid position and elimination of central fixation.

In a preferred vision assessment procedure, the vision of a subject is assessed using the automated method 100 with the system 200. Generally, the environmental conditions for the procedure should be office lighting with minimum noise. For example, windows should be covered by curtains because sunshine may affect the tracking effect of the eye tracker 50. Some models of eye trackers 50 produce optimum results under office lighting. There should be minimum noise because noise may be distractive for the subject. The chair whereon the subject is seated should be adjustable so that the subject can adjust himself/herself to directly face the eye tracker 50.

During the first stage 220 or process 120, the preliminary assessment 122 is performed on the subject's eye to estimate vision impairment based on fundus analysis. Based on this estimated vision impairment, a vision assessment test is customized/personalized for the subject. A set of customized test patterns 10 is determined from the pattern database 40 for the subject. As an example, the customized test patterns 10 follow that of MP, i.e. white dots on a black background, as shown in FIG. 3A to FIG. 3D.

During the second stage 240 or process 140, the eye tracker 50 is used for detecting the eyes of the subject and collecting the gaze data 20. Successful detection of the eyes facilitates the calibration process 144. As the gaze data 20 for each eye is collected separately, the calibration process 144 is performed for each eye, i.e. monocular calibration.

Figure 6:
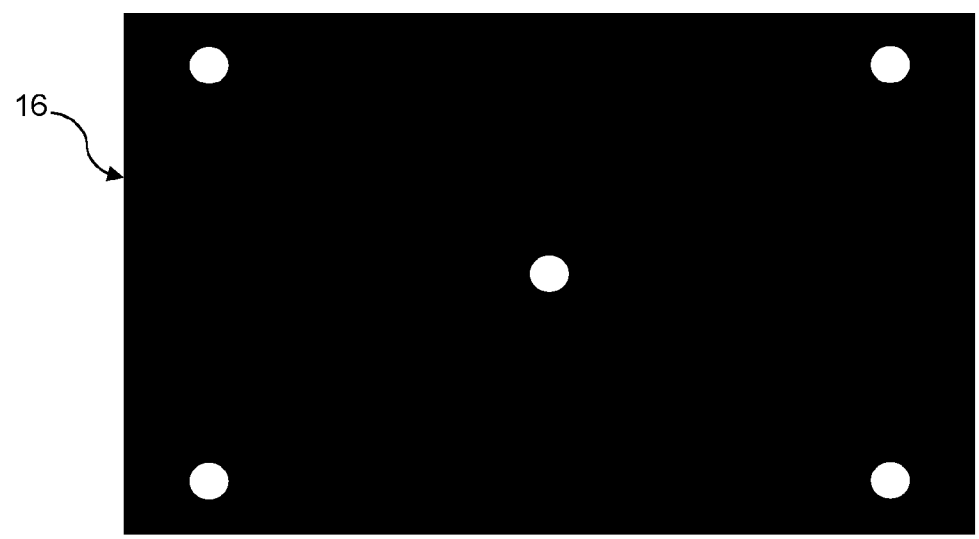
FIG. 6 illustrates a calibration pattern for a calibration process.

If there is not a calibration file of the participant, the calibration process 144 is necessary to be performed beforehand. If there is already a calibration file for the subject, the calibration file can be loaded to the eye tracker 50. A calibration setting with 5 points may be adopted. A calibration pattern or image 16 with the 5-point calibration setting is shown in FIG. 6. The calibration pattern 16 shows the 5 points as white dots on a black background, similar to the customized test patterns 10. This is because the eye tracker 50 achieves better performance when the same settings, e.g. colour and brightness, are adopted for the calibration process 144 and tracking of the customized test patterns 10. The 5 points of the calibration pattern 16 are displayed to the subject randomly and sequentially, i.e. one random point at a time. The subject is required to fixate on each point and calibration gaze data will be collected and used to calculate the calibration parameters. If the subject fails to fixate on any of the points, the 5-point calibration setting may need to be reconfigured. The calibration process 144 is performed on one eye at a time until all 5 points are successful. The calibration results for both eyes are then consolidated or merged to obtain the calibration parameters for the subject.

The second stage 240/process 140 further includes determining a threshold of the subject's gaze. A pattern such as or similar to the calibration pattern 16 is displayed to the subject. Specifically, each of the 5 points of the calibration pattern 16 as shown in FIG. 6 is sequentially displayed to the subject. The positions of the 5 points are (0.1, 0.1), (0.1, 0.9), (0.5, 0.5), (0.9, 0.1), and (0.9, 0.9), wherein (0, 0) refers to the left top corner and (1, 1) refers to the right bottom corner. The subject is required to fixate on each point and calibration gaze data will be collected and the average of the accuracies at the 5 points is used as the gaze threshold.

The second stage 240/process 140 further includes determining a suitable size of a test dot in a test pattern. A cross is first displayed at the centre of the screen 52. The eye tracker 50 then attempts to detect the subject's gaze and analyze whether the subject is fixating on the cross. If no, the eye tracker 50 reattempts until the subject's gaze is successfully detected. Once the eye tracker 50 detects that the subject is fixating on the cross, a test dot is displayed at a random position within 2-6 degrees of vision angle from the cross. The eye tracker 50 then attempts to detect the subject's gaze and analyze whether the subject is fixating on the test dot. If the subject notices the test dot, the suitable size of the test dot is detected as the current size. If the subject does not notice the test dot, the size of the test dot increases by 1 pixel and the eye tracker 50 reattempts to detect whether the subject notices the enlarged test dot.

After the calibration process 144 and determining the gaze threshold and test dot size, one or more vision assessment tests is performed and gaze data 20 from the tests are collected during the second stage 240/process 140. In one embodiment, the vision assessment tests include a MP test, a PHP test, and a Verification test.

The MP test uses the customized test patterns 10 with 33 points as an example. The procedure of the MP test is as follows.

a. The subject is seated before the eye tracker 50. The subject adjusts his/her position to make sure that the eyes are facing at nearly the centre of the screen 52.
 b. The eye tracker 50 tracks the position of the eyes and gaze in real time.
 c. Display a test pattern 10 with a cross at the centre and the subject is required to fixate on the cross.
 d. The subject is required to maintain his/her head in a fixed position during the displaying of the test patterns 10.
 e. Choose a position of the vision field to be tested.
 f. Select a random point (test dot) from the 33 points to be tested.
 g. Calculate the position of the test dot according to eye position, gaze position, and the position of the vision field to be tested (presented as two angles).
 h. Display the test dot on the screen 52.
 i. Wait for the subject's response (gaze shift) or until termination criteria (maximum display duration) is reached.
 j. The subject responds by pressing a key/button if he/she notices the appearance of the test dot.
 k. The test is ended after all the positions of the test dots (from the 33 points) have been tested.
 l. If not, display a cross at the position of the current test dot and return to step (c).

Figure 3D:
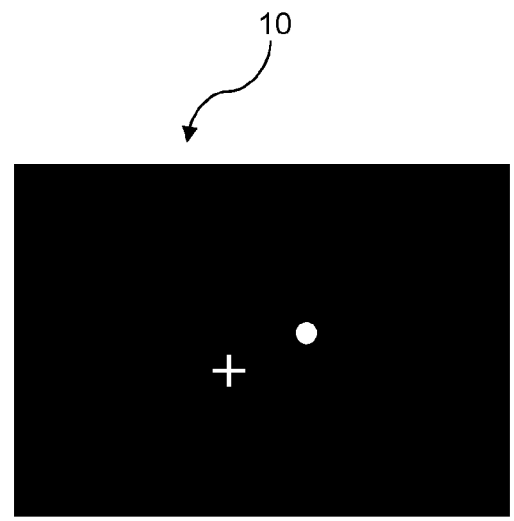

Thus, in the MP test, while the subject is fixating on the cross, a test dot is displayed each time and the gaze data 20 is collected and analyzed to determine if the subject notices the test dot. The cross is not always at a fixed position such that there is no central fixation. The gaze data 20 collected from the MP test is thus associated with a shifting of the subject's gaze from the cross to the test dot of each test pattern 10 (e.g. as shown in FIG. 3D). The cross may also be referred to as a base position and the test dot may also be referred to as a target position of the test pattern 10. As a cross is displayed at the position of the current test dot, the target position of a test pattern 10 is the base position of a succeeding test pattern 10.

The PHP test uses the customized test patterns 10 with 33 points as an example. The procedure of the MP test is as follows.
  a. The subject is seated before the eye tracker 50. The subject adjusts his/her position to make sure that the eyes are facing at nearly the centre of the screen 52.
  b. The eye tracker 50 tracks the position of the eyes and gaze in real time.
  c. Display a test pattern 10 with a base dot at the centre and the subject is required to fixate on the base dot.
  d. The subject is required to maintain his/her head in a fixed position during the displaying of the test patterns 10.
  e. Choose a position of the vision field to be tested.
  f. Select a random point (test dot) from the 33 points to be tested.
  g. Calculate the position of the test dot according to eye position, gaze position, and the position of the vision field to be tested (presented as two angles).
  h. Display a line of dots with a bump at the position of the test dot.
  i. Wait for the subject's response (gaze shift) or until termination criteria (maximum display duration) is reached.
  j. The subject responds by pressing a key/button if he/she notices the appearance of the bump.
  k. The test is ended after all the positions of the test dots (from the 33 points) have been tested.
  l. If not, display a base dot at the position of the current test dot.
  m. The base dot is then shifted to the centre of the screen 52, guiding the subject's gaze back to the centre of the screen 52.
  n. Return to step (c).

Thus, in the PHP test, while the subject is fixating on the base dot, a line of dots with a bump is displayed each time and the gaze data 20 is collected and analyzed to determine if the subject notices the bump. The base dot is not always at a fixed position such that there is no central fixation. The PHP test is thus similar to the MP test except for the difference in test pattern.

The Verification test is a tracking test which displays a series of the customized test patterns 10 such that a test dot appears to move on the screen 52 along a specified trajectory or path. The subject is required to follow the test dot with his/her gaze. The size of the test dot is same as the one determined previously. The trajectory of the test dot may be of a sine wave profile. The speed is variable but a typical value of 5 pixels per millisecond may be used. At each position of the test dot along the trajectory, the dot is maintained at the position for approximately 0.01 seconds.

There may be some limitations set for the vision assessment tests so that the duration of the tests does not go beyond a predefined time frame. As an example, the maximum number of tries is set as 3. If the eye tracker 50 cannot detect if the subject is fixating on the cross or dot, the eye tracker 50 will reattempt until the maximum number of tries. The maximum display duration is set as 3 seconds for the subject to fixate on the cross or dot. The minimum fixation duration is set as 1 second so that the eye tracker 50 detects that the subject has noticed the cross or dot if the subject has been fixating on the cross or dot for 1 second.

It will be appreciated that there may be additional tests in the vision assessment tests to better assess the vision functionality/impairment of the subject. For example, the vision assessment tests may include an additional a second MP test.

Each vision assessment test includes multiple events and each event is evaluated to determine if the subject gazed at the target. An event consists of target presentation and the subsequence gaze measurement. For example, one presentation of the fixation target (e.g. cross) with the gaze measurement is considered as one event. The subsequent presentation of another fixation target (e.g. test dot) is also another event with the corresponding gaze data 20. If the eye tracker 50 has a frame rate of 300 Hz, there will be around 300 gaze samples per second. The accuracy and precision are calculated as follows by considering all the gaze samples for the event.

Let E be an event, n be the number of events, $g_{ij}$ be the detected two-dimensional (2D) gaze position of the jth gaze sample of the ith event, $p_{ij}$ be the "true" position of the gaze, which is the position of the test dot (or cross) displayed on the screen 52. The accuracy $a_i$ and precision $p_i$ of the event $E_i$ are calculated as:

$$a_i = \frac{1}{n_i} \sum_{j=1}^{n_i} \|g_{ij} - p_{ij}\|_2$$

$$p_i = \frac{1}{n_i} \sum_{j=1}^{n_i} \|g_{ij} - \bar{g}_i\|_2$$

where $n_i$ is the number of gaze samples of the event $E_i$, $\bar{g}_i$, is the average of $g_{ij}$, $j=1,2,3, \ldots, n_i$, and $\|\cdot\|_2$ is L-2 norm.

After collecting the gaze data 20 in the second stage 240, the third stage 260 or process 160 compares the gaze data 20 with the subject database to estimate the vision functionality. The gaze-based functionality prediction model estimates the vision functionality of the subject based on the analysis of the gaze data 20. A vision assessment report or results 30 is/are generated and this provides details on any vision impairment of the subject. Additionally, the subject database may be updated with the gaze data 20 which may be used to train and improve the gaze-based functionality prediction model.

The automated method 100 and system 200 (also known as the AVIGA system) are able to perform vision assessment for subjects, such as for screening of AMD. The AVIGA system is personalized as customized test patterns 10 are determined for each subject according to his/her conditions and/or requirements. The AVIGA system is adaptive to the subject's gaze as there is no central fixation—the subject's gaze is detected using the eye tracker 50 and the customized test patterns 10 are displayed adaptively according to the position of the subject's gaze. The gaze of the subject in the presence of visual stimulus is recorded and analyzed to map out the position of a scotoma in the subject's vision. In this way, the AVIGA system avoids the need for verbal communication or manual response which is subjective and may cause errors. By obviating the subject's verbal communication/manual response, the AVIGA system can produce more objective results. Less manual effort is required from the subject so there is less fatigue caused to the subject, making it more relaxing for the subject to undergo vision assessment by the AVIGA system. Furthermore, the AVIGA system is easy to use as it is largely automated, as evident by the automated method 100. The AVIGA system can be operated automatically and independently by a trained nurse instead of a doctor or ophthalmologist. Consequently, there will be savings in the time and labour of the clinicians if the AVIGA system is implemented in a medical facility, e.g. hospital or clinical setting/environment. Due to its automation and ease of use, the AVIGA system may be implemented in a home setting/environment for subjects to operate independently and perform vision self-assessment.

In the foregoing detailed description, embodiments of the present disclosure in relation to an automated method and system for vision assessment of a subject are described with reference to the provided figures. The description of the various embodiments herein is not intended to call out or be limited only to specific or particular representations of the present disclosure, but merely to illustrate non-limiting examples of the present disclosure. The present disclosure serves to address at least one of the mentioned problems and issues associated with the prior art. Although only some embodiments of the present disclosure are disclosed herein, it will be apparent to a person having ordinary skill in the art in view of this disclosure that a variety of changes and/or modifications can be made to the disclosed embodiments without departing from the scope of the present disclosure. Therefore, the scope of the disclosure as well as the scope of the following claims is not limited to embodiments described herein.

What is claimed is:

1. An automated method for vision assessment of a subject, the method comprising:
   determining a set of test patterns for the subject based on a preliminary assessment of an eye of the subject, the preliminary assessment comprising fundus analysis to estimate vision impairment of the eye;
   displaying the set of test patterns sequentially to the subject;
   collecting data on the subject's gaze in response to each test pattern displayed to the subject, the collecting data comprising tracking the subject's gaze shifting in response to each test pattern; and
   assessing vision functionality of the subject based on the collected gaze data associated with the shifting of the subject's gaze.

2. The method according to claim 1, further comprising calibrating the eye before the preliminary assessment of the eye.

3. The method according to claim 1, wherein the fundus analysis comprises:
   imaging a fundus of the eye; and
   analyzing the fundus to detect damage and/or anomalies in the eye.

4. The method according to claim 1, wherein the set of test patterns is determined from a pattern database of predefined test patterns for assessing vision functionality/impairment.

5. The method according to claim 1, wherein assessing the vision functionality of the subject comprises determining time taken for the shifting of the subject's gaze.

6. The method according to claim 1, wherein each test pattern is displayed according to a current position of the subject's gaze.

7. The method according to claim 1, wherein assessing the vision functionality of the subject comprises comparing the gaze data with a subject database.

8. The method according to claim 1, wherein the subject's head is maintained in a fixed position during the displaying of the test patterns.

9. The method according to claim 1, the subject's gaze shifts from a base position to a target position of each test pattern.

10. The method according to claim 9, wherein the target position of a test pattern is the base position of a succeeding test pattern.

11. A system for vision assessment of a subject, the system comprising a processor configured for performing steps comprising:
    determining a set of test patterns for the subject based on a preliminary assessment of an eye of the subject, the preliminary assessment comprising fundus analysis to estimate vision impairment of the eye;
    displaying the set of test patterns sequentially to the subject;
    collecting data on the subject's gaze in response to each test pattern displayed to the subject, the collecting data comprising tracking the subject's gaze shifting in response to each test pattern; and
    assessing vision functionality of the subject based on the collected gaze data associated with the shifting of the subject's gaze.

12. The system according to claim 11, the steps further comprising calibrating the eye before the preliminary assessment of the eye.

13. The system according to claim 11, wherein the fundus analysis comprises:
    imaging a fundus of the eye; and
    analyzing the fundus to detect damage and/or anomalies in the eye.

14. The system according to claim 11, wherein the set of test patterns is determined from a pattern database of predefined test patterns for assessing vision functionality/impairment.

15. The system according to claim 11, wherein assessing the vision functionality of the subject comprises determining time taken for the shifting of the subject's gaze.

16. The system according to claim 11, wherein each test pattern is displayed according to a current position of the subject's gaze.

17. The system according to claim 11, wherein assessing the vision functionality of the subject comprises comparing the gaze data with a subject database.

18. The system according to claim 11, wherein the subject's head is maintained in a fixed position during the displaying of the test patterns.

19. The system according to claim 11, wherein the subject's gaze shifts from a base position to a target position of each test pattern.

20. The system according to claim 19, wherein the target position of a test pattern is the base position of a succeeding test pattern.

* * * * *